US006166546A

United States Patent [19]
Scheihing et al.

[11] Patent Number: 6,166,546
[45] Date of Patent: Dec. 26, 2000

[54] METHOD FOR DETERMINING THE RELATIVE CLAY CONTENT OF WELL CORE

[75] Inventors: Mark H. Scheihing, Richardson; Gary Lee White, Dallas; James D. Klein, Lucas, all of Tex.

[73] Assignee: Atlantic Richfield Company, Chicago, Ill.

[21] Appl. No.: 09/394,633

[22] Filed: Sep. 13, 1999

[51] Int. Cl.[7] .............................. G01V 3/06; E21B 49/00
[52] U.S. Cl. ....................................... 324/376; 73/152.11
[58] Field of Search .................................. 324/341, 376, 324/377; 436/25, 30, 31; 73/152.11

[56] References Cited

U.S. PATENT DOCUMENTS

| | | | |
|---|---|---|---|
| 4,099,118 | 7/1978 | Franklin et al. | 324/61 R |
| 4,876,512 | 10/1989 | Kroeger et al. | 324/376 |
| 5,457,394 | 10/1995 | McEwan | 324/642 |

OTHER PUBLICATIONS

"Dielectric Properties of Clay Suspensions in MHz to GHz Range", R. Raythatha and P. N. Sen, *Journal of Colloid and Interface Science*, vol. 109, No. 2, Feb. 1986.

SPE24675 "Electrical Impedance Variation With Frequency in Shales and Shaly Sands" by P.S. Adisoemarta and S.L. Morriss, University of Texas, Society of Petroleum Engineers, Inc., 1992.

"Geometrical Effects in the Dielectric Response of Partially Saturated Sandstones", R.J. Knight and A. Nur, *The Log Analyst*, Nov.–Dec., 1987, pp. 513–519.

"A Model for the Determination of Water Saturation from Dielectric Permittivity Measurements", M. M. Sherman, Amoco Production Company, *The Log Analyst*, May–Jun., 1987, pp. 282–288.

"The Effect of Rock/Water Interaction in Modelling the Dielectric Response of Sandstones", R. Knight and A. Endres, SPWLA Thirtieth Annual Logging Symposium, Jun. 11–14, 1989, pp. 1–19.

"The Effect of Level of Water Saturation on the Dielectric Constant of Sandstones", R. Knight and A. Nur, SPWLA Twenty–Fifth Annual Logging Symposium, Jun. 10–13, 1984, pp. 1–16.

"Basics of Measuring the Dielectric Properties of Materials", Application Note 1217–1, Hewlett–Packard Company, U.S.A. Mar. 1992, 5091–3300E.

"Taking the Measure of Moisture Meters", John Sillick, *Fine Woodworking*, Mar.–Apr. 1994, pp. 70–74.

"Solutions for Measuring Permittivity and Permeability", Hewlett Packard, U.S.A. Oct. 1993, 5091–9052E.

"Water Conductivity and Saturation Effects on the Dielectric Response of Shaly Sands"; Olivar A.L. De Lima and Mukul M. Sharma; SPWLA 32nd Annual Logging Symposium, Jun. 16–19, 1991.

"Modeling of the Dielectric Logging Tool at High Frequencies: Theory"; Weng Cho Chew, IEEE Transactions on Geoscience and Remote Sensing, vol. 26, No. 4, Jul. 1988.

"Measuring the Dielectric Constant of Solid Materials"; Hewlett Packard, Application Note 339–13, Japan, Oct. 1989, 5950–2390.

*Primary Examiner*—Christine K. Oda
*Assistant Examiner*—Henry S. Andersen
*Attorney, Agent, or Firm*—Robert E. Sloat; F. Lindsey Scott

[57] ABSTRACT

A method for determining a relative clay content of at least a portion of a well core taken from a subterranean geologic formation by: determining the relationship of the clay content of the well core portion to the dielectric constant of the well core portion at a selected frequency at relatively few locations over a substantial length of the well core portion by measuring the clay content by a clay determination test such as x-ray diffraction, thin section analysis, sieve analysis or laser particle analysis and the dielectric constant at the locations; and, measuring the dielectric constant of the well core portion at a large plurality of spaced apart other locations on the well core portion at the selected frequency; translating the large plurality of dielectric measurements according to the relationship into relative clay content measurements. The dielectric constant is representative of the water constant of the well core portion, which is related to the clay content of the well core portion.

8 Claims, 1 Drawing Sheet

METHOD FOR DETERMINING THE RELATIVE CLAY CONTENT OF WELL CORE

FIELD OF THE INVENTION

This invention relates to a method for determining the clay content of a subterranean geologic formation, and, more particularly, to a method for determining the clay content of a well core, or portion thereof, taken from a wellbore that penetrates that formation.

BACKGROUND OF THE INVENTION

Among the petrophysical properties of subterranean geologic formations that serve as hydrocarbon (crude oil and/or natural gas) reservoirs, porosity, water saturation, and permeability are the most important properties. Porosity and water saturation determine the volume of hydrocarbons that might be present in a given formation since the hydrocarbon content equals the porosity times one minus water saturation. Permeability determines the rate at which hydrocarbons can be produced from the formation rock. These three properties are all influenced by the presence of clay minerals in the formation.

Clay in a formation can cause reductions in porosity and permeability as well as complicate the determination of water saturation of the formation. Because of the influence of clay on these petrophysical properties, the determination of clay content of hydrocarbon-bearing subterranean formations is a critical step in their evaluation. Clay content is normally determined using wireline logs that respond to the high level of radioactivity associated with many clay minerals or to their effects on neutron and density logs. The interpretation of these logs provides a means of determining relative amounts of clay, but measurements on a well core taken from the formation are required to obtain quantitative data for calibration of such logs. Logs in general, and wireline logs in particular, are well known in the art. For example, see "Essentials of Modern Open-Hole Log Interpretation" by J. T. Dewan, PennWell Publishing Co., Tulsa, Okla., 1983.

Clay can exist in sedimentary formation rocks in a wide variety of forms and types. Clay content can be estimated by visual observation of a well core, or a sample therefrom, that has been taken from a formation, but such a determination is purely qualitative and not suitable for the calibration of wireline log models. Clay present as dispersed minerals in sandstone or carbonate rock is particularly difficult to determine by the naked eye. Quantitative determination of the clay content and clay mineralogy can be carried out using analytical techniques such as X-ray diffraction, mineral grain counts of thin, translucent sections of the well core, i.e., thin sections, and the like. These techniques are time-consuming, expensive, represent only a small formation volume, and are destructive of the well core sample. Because of these limitations, these techniques are often not obtained with sufficient data points for log model calibration.

Clay minerals have a large surface area relative to other rock-forming minerals. The surface properties of clays are such that they retain a few monolayers of bound water even after the movable water and other liquids have been removed from the pores and capillaries of the well core sample. Some clay minerals such as smectite contain water bound up as part of the mineral lattice itself. So, the retention of bound water by clays is much more pronounced than with that of non-clay minerals normally found in hydrocarbon-bearing formations. The different types of clays retain varying amounts of bound water after the movable water has been removed from the well core. Thus, even after a well core has been dried there will continue to be small amounts of bound water present in association with the clay minerals in the well core, and the amount of such bound water will vary with the type of clay mineral to which it is bound. Therefore, the measurement of the relative water content along a well core or portion thereof is an indirect indicator of the clay content thereof and even of the types of clay minerals therein.

The dielectric constant of rocks is influenced by their water content so that dielectric constants can be made to provide an indirect measurement of the clay content of a well core or portion thereof. Since the water content of various clays varies with the clay mineralogy, dielectric constants can be used as an indirect indicator of clay types present as well. For example, a clay such as kaolinite which has a relatively low surface area for a clay mineral has relatively small amounts of bound water for a clay, whereas smectite, which has a high surface area, retains larger amounts of bound water. Therefore, after the removal of all or essentially all of the movable water from the well core, and at the same ambient relative humidity around the well core, formation rock in the well core with a higher clay content will have a higher bound water content than formation rock in the well core that has a lower clay content, and rocks with a low clay content will have more bound water than non-clay rocks. Dielectric constants are well known in the art. For example, see "Well Logging for Physical Properties" by J. R. Hearst and P. H. Nelson, McGraw-Hill Book Co., New York, 1985.

SUMMARY OF THE INVENTION

According to this invention there is provided a method for determining the relative clay content of as least a portion of a well core, said well core having been taken from a subterranean geologic formation, by employing the measurement of dielectric constant characteristics of such well core or portion thereof and converting those dielectric constant measurements to clay content measurements using a standard regression technique in the manner disclosed hereinafter in detail.

DESCRIPTION OF THE PREFERRED EMBODIMENTS

Figure 1:
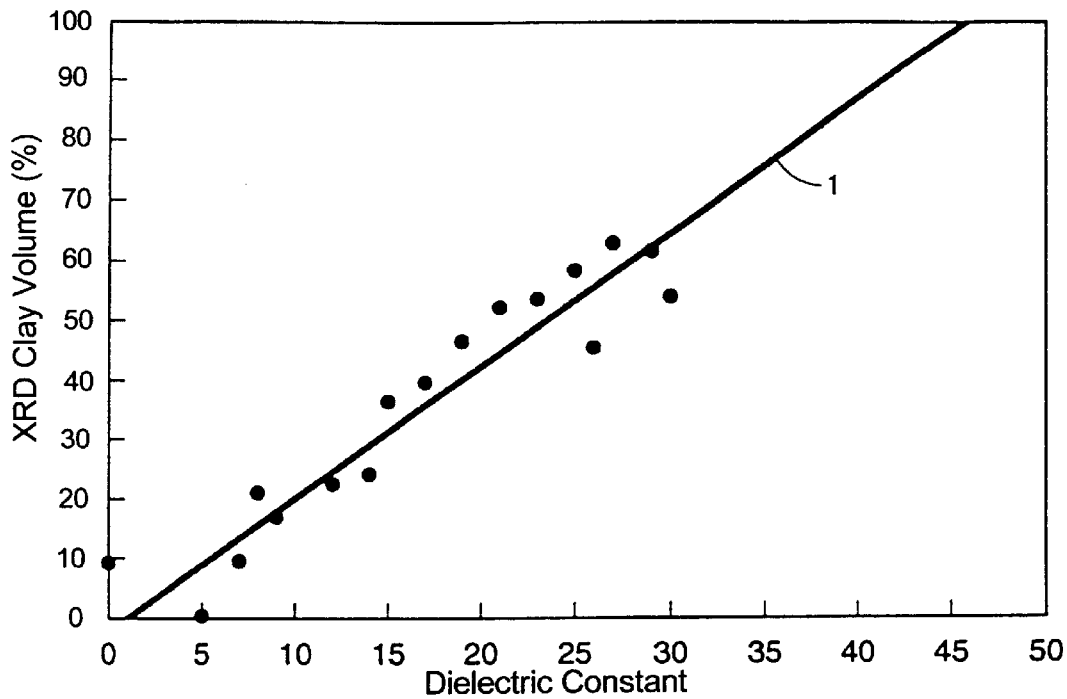
FIG. 1 shows the results of a regression analysis determination of the general relationship of the clay content of a well core to the dielectric constant characteristics of the same well core.

A well core taken from a well bore is normally tens or hundreds of feet long, and about two to four inches in diameter. The well core is normally cut along its long axis to provide two slabs, one containing about two-thirds of the core and the other one-third of the core. The two-third size slab sometimes has round plugs from about three-quarter to one inch in diameter taken therefrom for more detailed analysis. The one-third size slab is broken into samples three to six feet long and each sample is stored in an individual box for easy access for additional analysis.

In the discussion hereinafter and in the claims hereto, reference to a well core means essentially the entire core, whereas reference to a "portion" of a well core covers any smaller part of the well core. For example, a portion of a well core can be a "core sample" which is normally one to a few feet of the well core such as one or more boxes containing the one-third size slab. A portion of a well core can also be a "core section" such as a one inch diameter plug taken from the two-third size slab or a three-quarter inch or thicker disk-shaped piece cut from the well core, or the like. The term "portion" also covers internal cavities in the well core such as the hole left in the well core after a one inch plug has been removed therefrom.

According to this invention there is provided a method for determining the relative, not absolute, clay content along or across a well core or a portion thereof using a plurality of dielectric constant measurements taken along the surface of the well core.

Accordingly, the method of this invention, contrary to other techniques mentioned hereinabove, can be carried out in a short time using an inexpensive hand held detector, and is nondestructive of the well core material. Because this invention yields quick, inexpensive measurements, a very large number of dielectric constant readings can be taken on even a small portion of the well core. Therefore, by the practice of the method of this invention, a very high level of detail of the variation of the clay content from point-to-point along or across a length of the well core can be easily and quickly obtained in a nondestructive manner. Such a level of detailed measurements can readily be used in the calibration of wireline logs.

The measurement results of the method of this invention are useful as well in estimating the permeability of the formation or portions thereof and in obtaining a geologic description of that formation, particularly as to the location and types of clay minerals distributed throughout the well core.

In the practice of this invention the determination of the general relationship of the clay content of the well core to the dielectric constant characteristics of the well core is necessary, but this can be accomplished with relatively few data points. Because it can be done with only a few data points x-ray diffraction or thin section analysis discussed hereinabove can be employed. Other techniques can also be used such as laser particle analysis or sieve analysis, but hereinafter, for sake of simplicity and clarity, only the x-ray diffraction technique will be referred to.

The general relationship of clay content to dielectric constant characteristics of the well core can be established by making as few as ten x-ray diffraction measurements of a well core of conventional length, and certainly by making no more than one such measurement in every three feet of core. Thus, for example, for a 100 foot well core, from ten to thirty x-ray diffraction measurements can be taken of the clay content along the length of the well core. Dielectric measurements are made at essentially the same locations as the x-ray diffraction measurement locations. By using standard regression analysis, x-ray diffraction measurements which are quantitative as to the clay content of the well core are plotted against the dielectric measurements which are representative of the water content of the well core and a regression curve defined as shown in FIG. 1. Standard regression analysis is well known in the art. It can be linear or non-linear as desired. A full and complete description of regression analysis is set forth in Data Reduction and Error Analysis for the Physical Sciences by Philip R. Benington, McGraw-Hill Book Co., New York, 1969, the disclosure of which is incorporated herein by reference.

Figure 2:
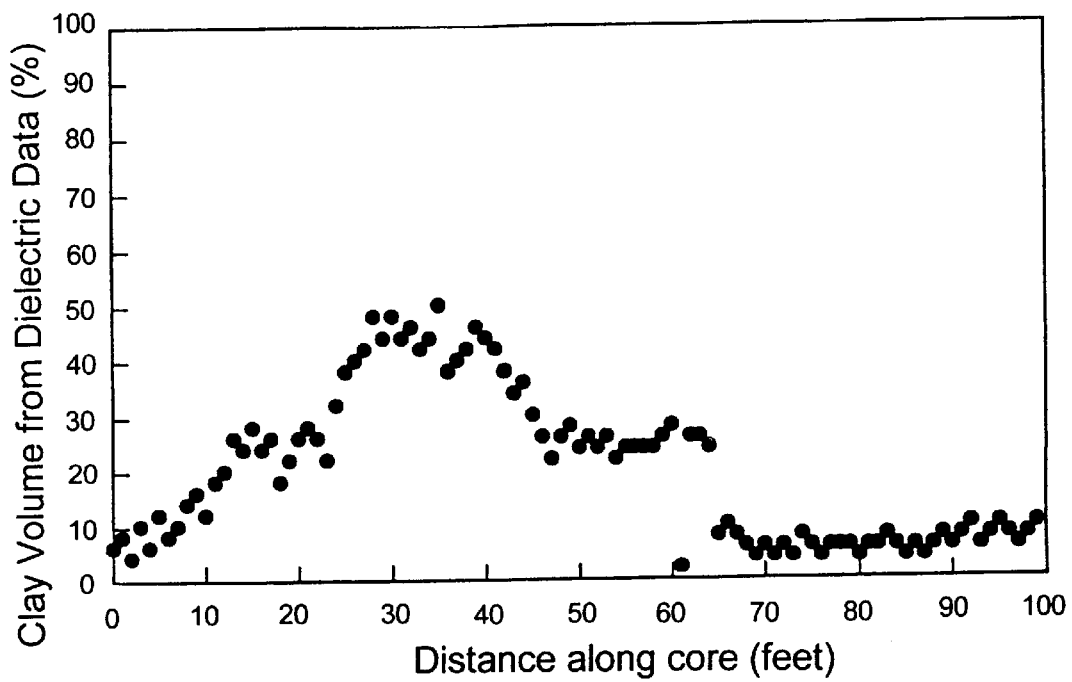
FIG. 2 shows clay volume content results achieved by use of dielectric constant measurements and the regression curve of FIG. 1.

Once the general relationship of the clay content to the dielectric constant characteristics has been established by obtaining a regression plot using a small number of x-ray diffraction measurements, a large number of dielectric measurements can be quickly and inexpensively made over all or any portion the the well core. Because the dielectric measurements are quick and easy to do they can be repeated as many times as desired to obtain a very high level of detail of the variation of clay content from point-to-point along or across the well core or any portion thereof. By using the regression curve of FIG. 1 all such dielectric constant measurements can readily be converted into a clay content determination and a plot made of the clay content as it varies along or across the well core as shown in FIG. 2. For example, whereas the general relationship of the clay content of the well core to the dielectric constant characteristics of the well core is determined using no more than one x-ray diffraction test for every three feet of well core and as few as ten x-ray diffraction tests no matter how long the well core, the dielectric constant measuring step of this invention will be at least one measurement for every two feet of well core up to as many as one measurement per inch of well core if that level of detail is desired. Thus, whereas ten to fifteen x-ray diffraction tests are used in this invention to obtain the desired regression analysis and plot shown in FIG. 1, in accordance with this invention literally hundreds to thousands of dielectric constant measurements can thereafter be made quickly and inexpensively and converted to clay content measurements using the regression curve of FIG. 1.

Thus, by the method of this invention, with the measurement of relatively few quantitative clay content data points by x-ray diffraction, a very large number of dielectric constant measurements can be quickly and inexpensively made and readily converted into clay content measurements. This greatly facilitates in an economic fashion the clay content analysis of the well core to any desired level of detail. This is especially true if the dielectric constant measurements are made with a hand-held device such as that disclosed in U.S. Pat. No. 4,099,118, issued to Franklin et. al. on Jul. 4, 1978, the disclosure of which is incorporated herein by reference. Of course, the method of this invention is also useful in an automated system which moves the well core or portion thereof past a stationary dielectric constant measuring device. Such a system will be readily obvious to those skilled in the art once apprised of the method of this invention and need not be disclosed here in detail. However, this method is most advantageously employed when the dielectric measurements are made with a hand-held device that can readily be moved to any location on the well core at any time desired.

The dielectric constant varies with the frequency by which the constant is measured. The constant is known to decrease with such frequency as well as increase with water content. For example, the dielectric constant of pure water is around 90. The first layer of water bound to a mineral surface has a lower value of around 6 to 8. Completely dry rocks have constants that range from 4 to 8, depending on their mineralogy. If water is added to a dry clay-bearing sandstone, the constant increases gradually until approximately four monolayers of water are present on the mineral grain surfaces. At that point, as additional water is added, the water is less affected by surface forces of the mineral grains, and the constant increases rapidly. Dielectric constant measurements made at low frequencies show enhanced dielectric properties in the presence of clays, due to the interactions between the charged surfaces of the clays and the polar water molecules. At higher frequencies the surface interactions disappear, and the response is strictly due to the dielectric properties of the water itself. Accordingly, in the practice of this invention the dielectric constant is measured using electrical energy oscillating at a predetermined, fixed frequency of from about 100 kiloHertz to about 10 gigaHertz, preferably from about 1 megaHertz to about 5 gigaHertz.

EXAMPLE

A one hundred foot sandstone well core having kaolinite and smectite clay minerals dispersed at various points along the length thereof is analyzed using the method of this invention. A hand held sensor employing a fixed frequency of one megaHertz is employed. Ten samples along the length of the two-thirds size slab of the 100 foot well core are subjected to destructive x-ray diffraction and ten dielectric constant measurements are made at essentially the same location on the well core from which the x-ray diffraction samples were taken. A standard linear regression analysis is conducted on these data points to obtain a regression plot like that shown in FIG. 1.

Thereafter, 500 dielectric constant measurements are made along the length of the one-third size slab of the 100 foot well core using the hand held dielectric sensor and these 500 data points are converted to clay content measurements using the regression plot of FIG. 1.

Reasonable variations and modifications are possible within the scope of this disclosure without departing from the spirit and scope of this invention.

What is claimed is:

1. In a method for determining a relative clay content of at least a portion of a well core, said well core having been taken from a subterranean geologic formation, the improvement comprising:

1. determining a relationship between a clay content of a well core portion and a dielectric constant of the well core portion at each of a relatively few locations over a substantial length of the well core portion by measuring the clay content and the dielectric constant at the locations, the dielectric constant being measured at a predetermined fixed frequency;

2. determining a dielectric constant measurement of the well core portion at a large plurality of additional spaced apart locations on the well core portion at the predetermined fixed frequency; and, 3. translating said large plurality of dielectric constant measurements into a large plurality of relative clay content measurements based upon the relationship.

2. The method of claim 1 wherein the relationship of clay content to dielectric constant determination is conducted one time; the measurement of a large plurality of dielectric constants is conducted a plurality of times over a plurality of different well core portions, and the translation is conducted a plurality of times for the plurality of different core portions using each time the relationship.

3. The method of claim 1 wherein the relationship of clay content to dielectric constant of step 1 is determined by one of x-ray diffraction and sieve analysis.

4. The method of claim 1 wherein the relationship of clay content to dielectric constant of step 1 is determined no more than once every three feet of well core.

5. The method of claim 1 wherein said predetermined, fixed frequency is in the range of from about 100 kilohertz to about 10 gigahertz.

6. The method of claim 1 wherein the dielectric constant measurements of step 2 are determined at least once every two feet of core portion.

7. The method of claim 1 wherein the dielectric constant is measured using a hand-held dielectric sensor.

8. The method of claim 1 wherein the dielectric constant is measured using an automated system that carries the well core portion past a stationary dielectric sensor.

* * * * *